United States Patent
Opahle et al.

[11] Patent Number: 5,885,235
[45] Date of Patent: Mar. 23, 1999

[54] JOINT BRACE AND MORE PARTICULARLY A KNEE BRACE

[75] Inventors: Hans Georg Opahle; Erich Albrecht, both of Rosenheim, Germany

[73] Assignee: Albrecht GmbH, Stephanskirchen, Germany

[21] Appl. No.: 801,587

[22] Filed: Feb. 18, 1997

[30] Foreign Application Priority Data

Feb. 19, 1996 [DE] Germany .................. 196 06 092.3

[51] Int. Cl.[6] .................................................. A61F 5/00
[52] U.S. Cl. .................................................. 602/16; 602/26
[58] Field of Search .................. 602/16, 20, 23, 602/26

[56] References Cited

U.S. PATENT DOCUMENTS

| | | |
|---|---|---|
| 2,883,982 | 4/1959 | Rainey et al. . |
| 3,732,862 | 5/1973 | Golia . |
| 4,088,130 | 5/1978 | Applegate ................................ 602/16 |
| 4,463,751 | 8/1984 | Bledsoe . |
| 4,686,969 | 8/1987 | Scott . |
| 5,000,169 | 3/1991 | Swicegood et al. ...................... 602/16 |
| 5,052,379 | 10/1991 | Airy et al. ................................ 602/16 |
| 5,135,469 | 8/1992 | Castillo .................................... 602/16 |
| 5,188,584 | 2/1993 | Petrofsky et al. ........................ 602/16 |
| 5,292,303 | 3/1994 | Bastyr et al. ............................. 602/16 |
| 5,399,154 | 3/1995 | Kipnis et al. ............................. 602/26 |
| 5,409,449 | 4/1995 | Nebolon ................................... 602/16 |
| 5,437,611 | 8/1995 | Stern ........................................ 602/16 |
| 5,443,444 | 8/1995 | Pruyssers .............................. 602/16 X |
| 5,460,599 | 10/1995 | Davis et al. .......................... 602/16 X |
| 5,520,627 | 5/1996 | Malewicz ................................. 602/26 |
| 5,611,773 | 3/1997 | Nash et al. .............................. 602/16 |
| 5,676,640 | 10/1997 | Biedermann ......................... 602/16 X |

FOREIGN PATENT DOCUMENTS 387595  1/1924  Germany .

OTHER PUBLICATIONS

Prospects of OMNI Scientific, Inc.

Primary Examiner—Linda C.M. Dvorak
Attorney, Agent, or Firm—Horst M. Kasper

[57] ABSTRACT

In the case of a joint brace with two splints (1 and 3) connected together in an articulating manner, an abutment (26) is provided on one splint (3), said abutment cooperating with a complementary abutment (25) on the other splint (1) for limiting the pivot angle. The complementary abutment (25) is provided on an angle setting element (18), which is pivotally mounted in relation to the splint (1) and may be set in different positions on such splint. By moving the angle setting element (18) in relation to the splint (1) the position of the complementary abutment (25) and accordingly the maximum pivot range of the splint (1) may be reset steplessly in a predetermined angular range.

19 Claims, 6 Drawing Sheets

JOINT BRACE AND MORE PARTICULARLY A KNEE BRACE

BACKGROUND OF THE INVENTION

1. Field of the Invention

The invention relates to a joint brace and more particularly a knee joint brace for preventing torsion of a distal extremity in relation to a proximal extremity connected therewith articulatingly.

2. Brief Description of the Background of the Invention Including Prior Art

Joint braces of this type are known as knee orthoses, and for example are applied following cruciate ligament operations, with the purpose of precluding a rotary movement of the lower leg in relation to the upper leg. The splints running along either side of the knee are joined together articulatingly at the level of the knee and at their free ends are firmly strapped to the upper and, respectively, lower leg. The rotary joint then permits flexion and extension of the leg for a certain, adjustable range of pivoting.

It is furthermore a practice to limit the range of pivoting of the splints and accordingly of the knee joint in a predetermined, variable fashion. This may for instance be done by the insertion of shims or wedges with different sizes between the abutment of one splint and the complementary abutment of the further splint connected therewith. A further practice is to insert an abutment pin in different holes in accordance with the desired range of pivoting, such holes being provided in one of the splints connected together.

In the case of these known joint braces it is a disadvantage that any increase or reduction in the free pivot range is only possible in relatively large angular steps. For example in the case of a conventional knee brace the limitation of the pivoting in the extension direction, i. e. in the stretch out direction of the extremities of the body, adjustment is only possible to set to four different positions, i. e. in 15° steps between 0° and 45°. The 0° setting then corresponds to the completely straight, extended position of the lower leg in relation to the upper leg. The U.S. Pat. No. 4,463,751 discloses a joint brace in accordance with the preamble of claim 1, in the case of which two interiorly placed, circular adjustment disks are employed having recesses for limiting the extension or, respectively, flexion of the distal splint. Pins extend through the recesses and move, together with the distal splint, within the recesses and in the respective end positions abut against abutment faces in the recesses.

Furthermore the U.S. Pat. No. 3,732,862 discloses a foot joint brace, which renders possible upward motion of the tip of the foot, whereas lowering thereof below a certain basic position is to be prevented. This known foot brace possesses a rotatably mounted pivot part with a lower abutment and a plurality of upper through holes in order to hold such pivot part by means of a setting pin at different angles of inclination in relation to a lower leg splint.

The U.S. Pat. No. 2,883,982 discloses a knee joint brace in the case of which two contacting faces on the distal and proximal splints are designed in the form of gear teeth and possess faces in rolling engagement with one another. In this case the extended position is limited by means of a tie, whose one end is secured within a slide recess means in the proximal splint and whose other end is pivotally secured to the distal splint. These last-named splints are however complex in design are furthermore expensive and are difficult to manipulate. Moreover, they are unsuitable for stretching the joint in question should its mobility be impaired owing to ligament surgery, injuries, inflammation and the like and the joint capsule and/or connective tissue be defective as regards extension or flexion.

SUMMARY OF THE INVENTION

1. Purposes of the Invention

Accordingly one object of the invention is to provide a joint brace of the type initially mentioned which while possessing the simplest possible structure allows the maximum range of variation as regards setting the limits of pivotal movement and also permits an extremely exact and simple manner of setting.

These and other objects and advantages of the present invention will become evident from the description which follows.

2. Brief Description of the Invention

In accordance with the invention this object is to be attained using the features of claim 1. Advantageous embodiments of the invention are described in the further claims.

In accordance with the invention the abutment element is adapted to be set in predetermined, different positions in a joint section, near the pivot axis, of one splint. Furthermore the complementary abutment adjustment element comprises a pivotal lever with a lever arm in the form of a handle or manipulating section, which extends past the joint section adjacent to the pivot axis and by means of a guiding and setting element, adapted to be slid within a slot means, may be secured to the splint associated with the complementary abutment setting element.

Owing to this design of the invention an additional possibility for adjustment for the limits of the range of pivoting is created, since it is not only possible for the abutment element to be secured in different positions on one of the splints, but furthermore the position of the complementary abutment may be changed in relation to the other splint. This means, in other words, that if the complementary abutment is engaged with the abutment element, a further change in the limit of pivoting may be caused if the splint bearing the complementary abutment adjustment element is again pivoted in relation to the complementary abutment adjustment element. This means that there are additional possibilities of adjustment: the limit of the range of pivoting for the distal splint in relation to the proximal splint may be changed in an extremely accurate, stepless manner and the joint and connective tissue may be stretched or hyperextended as far as an extremely accurately set limit. The additional adjustment may in this case be performed in an extremely simple fashion, since the manipulating section of the complementary abutment setting element is quite accessible and after release of the guiding and setting element may be pivoted manually in relation to the respective splint.

It is an advantage for the manipulating section of the complementary abutment adjustment element and the splint associated with it each to have a slot, the longitudinal axes of such slots intersecting at a predetermined angle. In this respect the guiding and setting element extends through the two slots in the overlapped parts thereof so that a displacement of the guiding and setting element necessarily produces a relative displacement between the complementary abutment adjustment element and the splint. In the case of this embodiment the guiding and setting element slides during the setting operation within the slots, a relatively long displacement stroke of the guiding and setting element producing a relatively small relative displacement between the complementary abutment setting element and the splint.

It is in this manner that the additional angular adjustment can be performed steplessly and extremely precisely and with a particularly fine degree of accuracy. Should the patient attempt to move the joint splint past the maximum pivot range, a major proportion of the forces will be taken up via the lateral limiting walls of the slots so that an accidental displacement of the guiding and setting element may be precluded even in the case of low gripping forces. Owing to the simple, stepless adjustment of the splint in relation to the complementary abutment setting element joints may be stretched with a particularly fine degree of accuracy to reach the desired limiting position.

A particularly advantageous design of the invention is characterized in that the range of adjustment of the splint in relation to the complementary abutment setting element amounts to 0° to −20°, and more particularly 0° to −15° in the extension direction, i. e. in the stretch direction of the extremities, as related to the angular position set by the abutment. This means that for example if the abutment element is located in its limiting extension setting of 0°, the maximum extension of the joint brace does not amount to 0°, which would correspond to the extended leg, but rather there is the possibility of a further change in angle of the complementary abutment in the extension direction so that a hyperextension of the lower leg of, at the most, −15° to, respectively, −20° is possible. Although such pronounced over-stretching is only required in a few exceptional cases a slight degree of over-stretch is being employed on an increasing scale, if for instance the other, healthy joint is itself subject to such over-stretch.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

In the accompanying drawings, in which are shown several of the various possible embodiments of the present invention.

DESCRIPTION OF INVENTION AND PREFERRED EMBODIMENT

Figure 1:
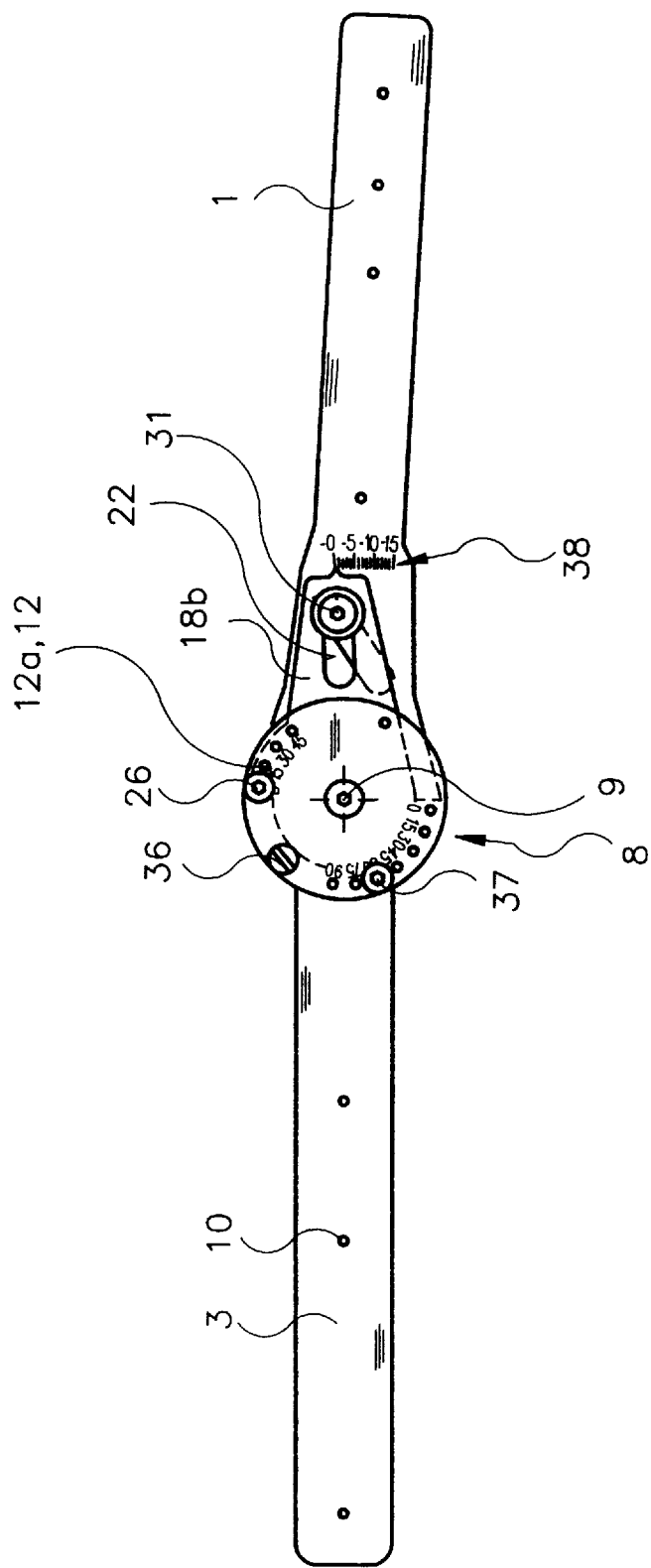
FIG. 1 shows a lateral view of the joint brace of the invention.

In the following the joint brace of the invention will be described with reference to FIGS. 1 through 7, two joint braces being employed in a normal case, which are arranged on opposite sides of the joint. The joint brace to be arranged on the opposite side of the joint is symmetrical in design. Attachment straps for the attachment of the joint brace to a proximal or, respectively, distal extremity are omitted in the FIGS. 1 through 6B in order to make the drawing more straightforward. The joint brace of the invention will be described with reference to a knee joint brace, although it may well be applied to other joints, as for example the elbow joint.

Figure 2:
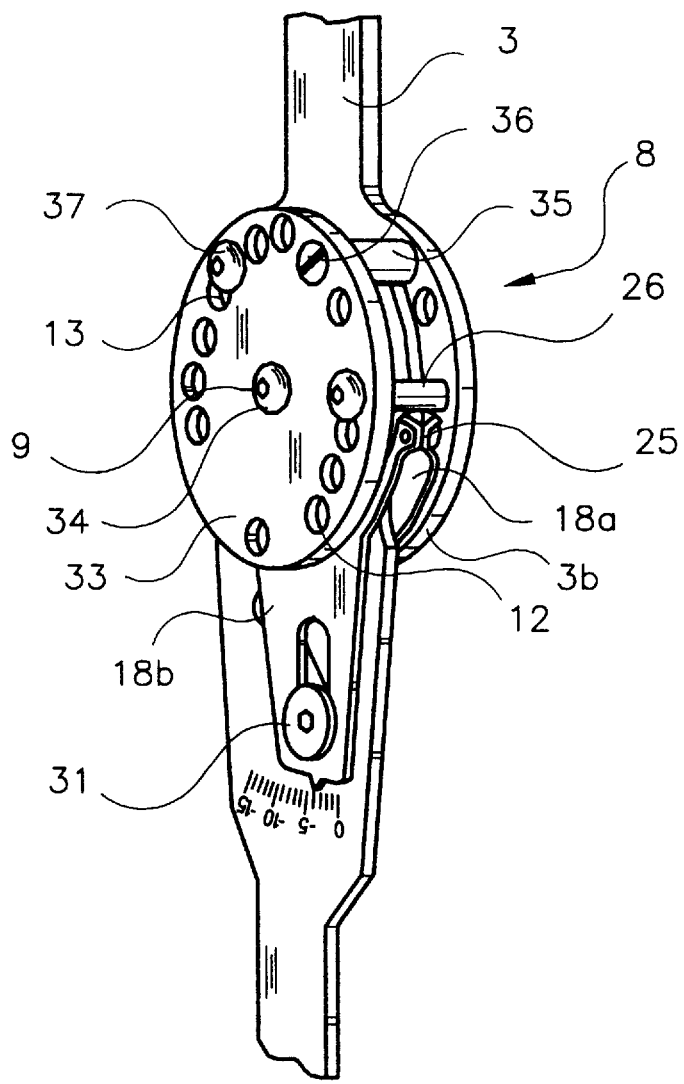
FIG. 2 is a perspective elevation of the joint region of the joint brace in accordance with FIG. 1.
Figure 3:
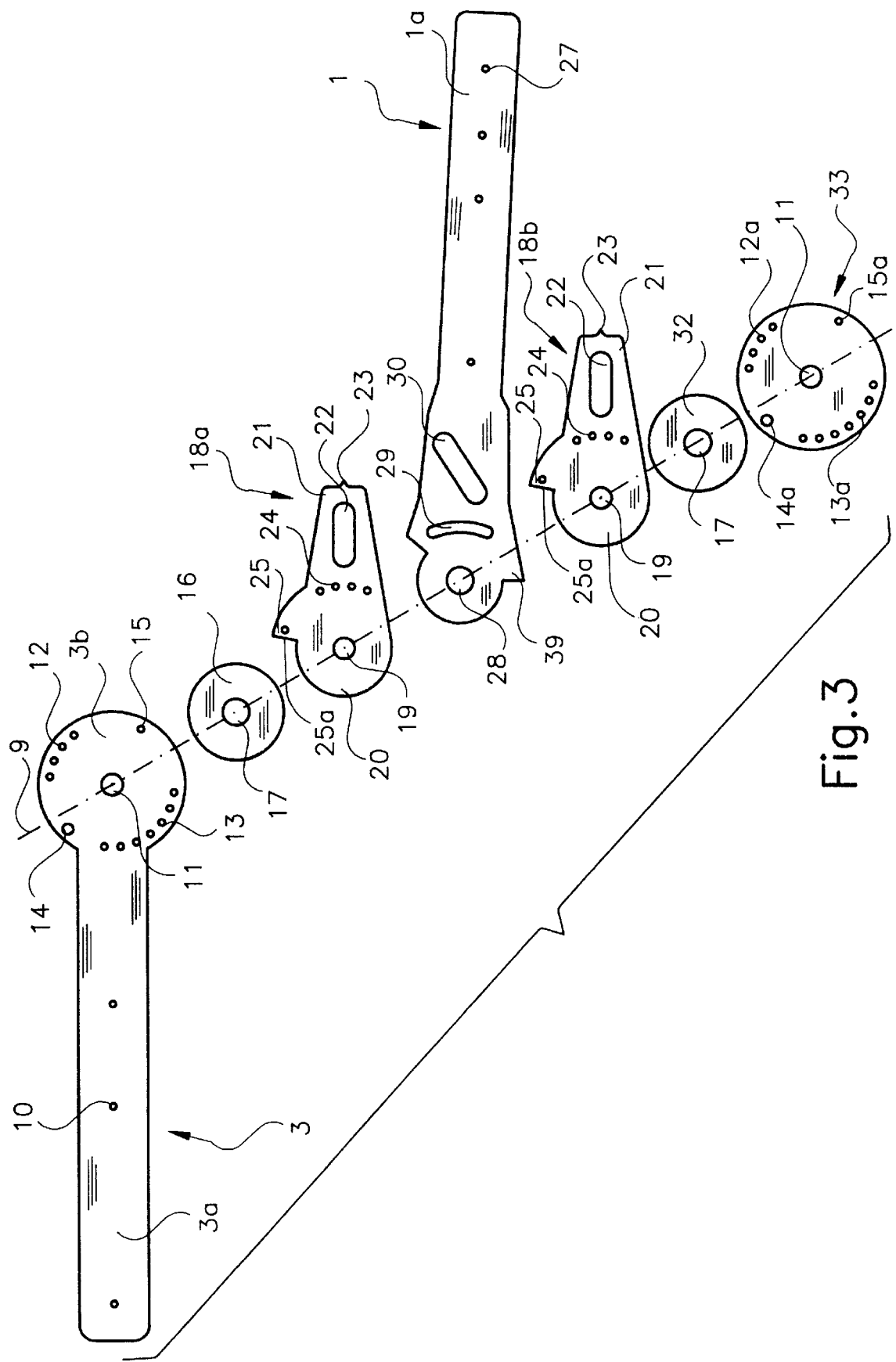
FIG. 3 shows a diagrammatic exploded view of the individual parts of the joint brace of FIG. 1.

As shown in FIGS. 1 through 3, the joint brace of the invention comprises a distal splint 1, which may be attached to the lower leg by means of a suitable straps, not illustrated, and a proximal splint 3, which may also be attached to the upper leg by means of straps, not illustrated and is connected by means of a rotary joint 8 in an articulating fashion with the distal splint 1. The pivot axis is in this case referenced 9.

The joint brace of the invention is represented in an exploded manner in FIG. 3 to indicate the main parts thereof. As is apparent, the proximal splint 3 comprises an elongated attachment section 3a and a joint section 3b in the form of a circular disk, which is integrally formed on one end of the attachment section 3a. In the attachment section 3a a plurality of through holes 10 are provided for the attachment of the straps, not illustrated.

In its center the joint section 3b in the form of a circular disk has a hole 11 for the passage of a joint pin, not illustrated. In the vicinity of the outer periphery there are furthermore four extension limiting holes 12, which are arranged adjacent to each other in the circumferential direction. In this case any two adjacent extension limiting holes 12 include an angle of respectively 15° between them.

On the other side of the central hole 11 there are in all seven flexion limiting holes 13, which are also arranged in the vicinity of the outer periphery of the joint section 3b and are arranged adjacent to one another in the circumferential direction. Any two adjacently placed flexion limiting holes 13 are again set at a distance apart of respectively 15°.

Between the extension limiting holes 12 and the flexion limiting holes 13 there is furthermore, generally at the same distance from the pivot axis 9, an attachment hole 14 for receiving an attachment screw, not illustrated. A stop hole 15 serves to receive a stop screw, not illustrated, if the pivotal movement of the proximal splint 3 in relation to the distal splint 1 is to be completely locked. All holes 12, 13, 14 and 15 are in the form of through holes and are generally located along a common circular path about the pivot axis 9.

The proximal splint 3 constitutes the part of the joint brace which is furthest to the inside and which accordingly directly contacts the upper leg of the patient with a suitable cushion in between.

As further shown in FIG. 3 there is a circular friction reducing washer 16 adjoining the joint section 3b of the proximal splint 3 on the outside thereof, such washer being for example in the form of a thin sheet of synthetic resin. The friction reducing washer 16 has a central through opening 17 for the passage of the pivot pin.

To the outside of this there then comes one half 18a of a complementary abutment setting element 18, which rests against the inner side of the distal splint 1. The other half 18b of the complementary abutment setting element 18 is, apart from a symmetrically arranged cavity to be described later, identical to the half 18a and on the opposite side of the distal splint 1 contacts the same.

Each complementary abutment setting element half 18a and 18b comprises a thin but nevertheless firm piece of steel sheet and more particularly of stainless steel and is pivotally mounted for movement around the pivot axis 9. For this purpose the complementary abutment setting element halves 18a and 18b possess a through opening 19, through which the rotary pivot pin may be received. The proximal end of the complementary abutment setting element halves 18a and 18b is designed in the form of a semicircular section 20, the radius of such semicircle being smaller than the radius of the circular arc, on which the extension limiting holes 12 and the flexion limiting holes 13 in the proximal splint 3 lie. These holes 12 and 13 are accordingly not covered over by the semicircular section 20 of the complementary abutment setting element halves 18a and 18b. It is convenient for the radius of the semicircular section 20 to be equal to that of the friction reducing washer 16.

Adjoining the semicircular section 20 of the complementary abutment setting element halves 18 and 18b there is an elongated manipulating section 21, which extends past the joint section 3b of the proximal splint 3 generally in the longitudinal direction of the distal splint 1. In this manipulating section 21 there is a slot 22 aligned with the longitudinal direction of the complementary abutment setting element halves 18a and 18b, the longitudinal axis of the slot intersecting with the axis of the pivot axis 9. The length of the slot 22 amounts to approximately three to four times its width. At the distal end of the manipulating section 21 there is a pointer 23, which is aligned with the longitudinal axis of the complementary abutment setting element halves 18 and 18b.

Between the slot 22 and the through opening 19 four stop holes 24 are provided arranged on an arc around the pivot axis 9, such holes being at an angular distance apart of 15°. The radius of this circular arc is equal to the radial distance of the stop hole 15 in the proximal splint 3 from the pivot axis 9 so that the stop hole 15 may, in certain angular settings, be aligned with the stop holes 24 and a stop sprag, not illustrated, may be put through them.

Adjoining the semicircular section 20 of the complementary abutment setting element halves 18a and 18b there is a counter-abutment 25, which in FIG. 3 is shown pointing upward, in the form of a spur projecting past the semicircular section 20. This spur extends in the radial direction past the extension limiting holes 12 to the outside so that a terminal contact face of the complementary abutment 25 may strike against a pin-like abutment element 26 (FIG. 3), such element 26 running through one of the extension limit holes 12. As shown in FIG. 2, it is possible for the spurs 25 of the two complementary abutment setting element halves 18a and 18b to be so dented toward one another and secured together by means of a rivet that they touch each other radially clear of the distal splint 1 and a corresponding transverse connection is produced. As an alternative it would be quite possible to provide a spacing sleeve or a spacing pin between the spurs 25 of the two complementary abutment setting element halves 18a and 18b in order to ensure a suitable mutual holding effect in this region.

As is furthermore particularly clearly indicated in FIG. 3, the distal splint 3 possesses an elongated attachment section 1a, in which in all four holes 27 are provided for attachment of straps, not illustrated. At the proximal end a through opening 28 is provided, through which the pivot joint pin can be inserted so that the distal splint 1 may be pivoted about the pivot axis 9. The proximal end is again designed generally to be semicircular, it being possible for the arc to extend for more than 180°, for example 220°. The radius of this semicircular section is again generally the same as that of the semicircular section 20 of the complementary abutment setting element halves 18a and 18b and the radius of the friction reducing washer.

On an arc centered on the pivot axis 9 an arcuate slot 29 is provided. Once the two complementary abutment setting element halves 18a and 18b are so aligned in relation to the distal splint 1 that the longitudinal axes of such parts are parallel to one another, this slot 29 will completely cover the stop holes so that the above mentioned stop screw, not illustrated, may be inserted for locking pivoting of the distal splint 1 in relation to the proximal splint 3.

Between the arcuate slot 29 and the attachment section 1a of the distal splint an obliquely set slot 30 is furthermore provided, whose longitudinal axis makes an angle of 34° with the longitudinal axis of the distal splint 1 in the illustrated embodiment of the invention. The length of the slot 30 may be slightly larger than that of the slot 22 of the complementary abutment setting element halves 18a, whereas the width thereof is preferably the same. The arrangement and the length of the slots 22 and 30 is so selected that a guiding and setting element 31, illustrated in more detail in FIGS. 4A through 6B, which is inserted through the slots 22 and 30, is located at the two limits of pivoting of the complementary abutment setting element 18 in relation to the distal splint 1 at the two ends of the slots 22.

As shown in FIG. 3 the outer side of the outer complementary abutment setting element half 18b adjoins a further friction reducing washer 32, which is of the same design as the friction reducing washer 16 and also has a through opening 17 for accepting the joint pin.

The laterally outer termination of the joint brace constitutes a threaded washer 33, indicated merely diagrammatically in FIG. 1, with extension limiting holes 12a, flexion limiting holes 13a, an attachment hole 14a and a stop hole 15a, which are opposite to and in line with the corresponding holes 12, 13, 14 and, respectively, 15 of the circular joint section 3b of the proximal splint 3. The number and arrangement of these holes 12a, 13a, 14a and 15a in relation to the pivot axis 9 is consequently identical to that of the holes 12, 13, 14 and, respectively, 15. The holes 12a, 13a, 14a and 15a are however furnished with an internal screw thread in order to be able to screw in screws or pins, whose shank parts adjacent to the head thereof have a screw thread. Furthermore the screw threaded washer 33, completely in the form of a circular disk, has the same radius and the same central through opening 11 for receiving the pivot pin as the circular joint section 3b of the proximal splint 3.

The pivot pin, not illustrated, may comprise a bushing-like part with an axial, through screw threaded hole, into which, after assembly of the parts illustrated in FIG. 3, two holding screws 34 (FIG. 2) can be screwed. In order to maintain the desired spaced out, parallel arrangement of the screw threaded disk 33 or washer in relation to the circular joint section 3b of the proximal splint 3, there is furthermore a distance sleeve 35 with a screw threaded axial through hole, which is arranged aligned with the attachment holes 14 and 14a of the joint section 3b and, respectively, of the threaded washer 33. Corresponding attachment screws 36, inserted from both sides into the attachment holes 14 and 14a may accordingly be screwed to the distance sleeve 35.

As furthermore indicated in FIG. 2, in the illustrated embodiment of the invention the pin-like extension abutment element 26 is inserted into the two opposite, uppermost extension limiting holes 12 and 12a, it being screwed by means of a short threaded section, adjoining the pin head, to the extension limiting, screw threaded hole 12a. Furthermore a flexion abutment element 37 is inserted into two opposite flexion limiting holes 13 and 13a so that flexion of the joint brace as far as 60° is rendered possible as will be explained in the following.

In the following with reference to FIGS. 4A through 6B the manner of functioning of the joint brace of the invention will be described in more detail. The respective figures, denoted A and, respectively, B, each show the joint brace in the same position and from the same side, but however differ to the extent that in the drawings marked B the screw threaded washer 33 and the friction reducing disk 33 are omitted in order to make the showing more straightforward. Furthermore, in this case the guiding and setting element 31 is illustrated in section.

In all of the FIGS. 4A through 6B the extension abutment element is inserted in the uppermost extension limiting hole 12 and 12a, which is referenced "0"°. The flexion abutment element 37 is respectively inserted in a flexion limiting hole 13 and 13a so that a maximum flexion of the lower leg in relation to the upper leg amounting to 60° is permitted. The guiding and setting element 31 in each case comprises a screw with a widened out screw head covering over the slot 22 in the complementary abutment setting element half 18b and a nut on the opposite side resting on the complementary abutment setting element half 18a in order to clamp together the two complementary abutment setting element halves 18a and 18b and to thrust same against the intermediately placed distal splint 1. In the screwed up state the complementary abutment setting element 18 is hence now not able to be pivoted in relation to the distal splint 1. If on the contrary the guiding and locking element 31 is slackened off, it may then be moved along the slots 22 and 30 with the result that a pivoting motion of the complementary abutment setting element 18 in relation to the distance splint 1 is rendered possible in an angular range of 0° to −15°. A reading may be taken for this relative angle on a scale 38.

Figure 4A:
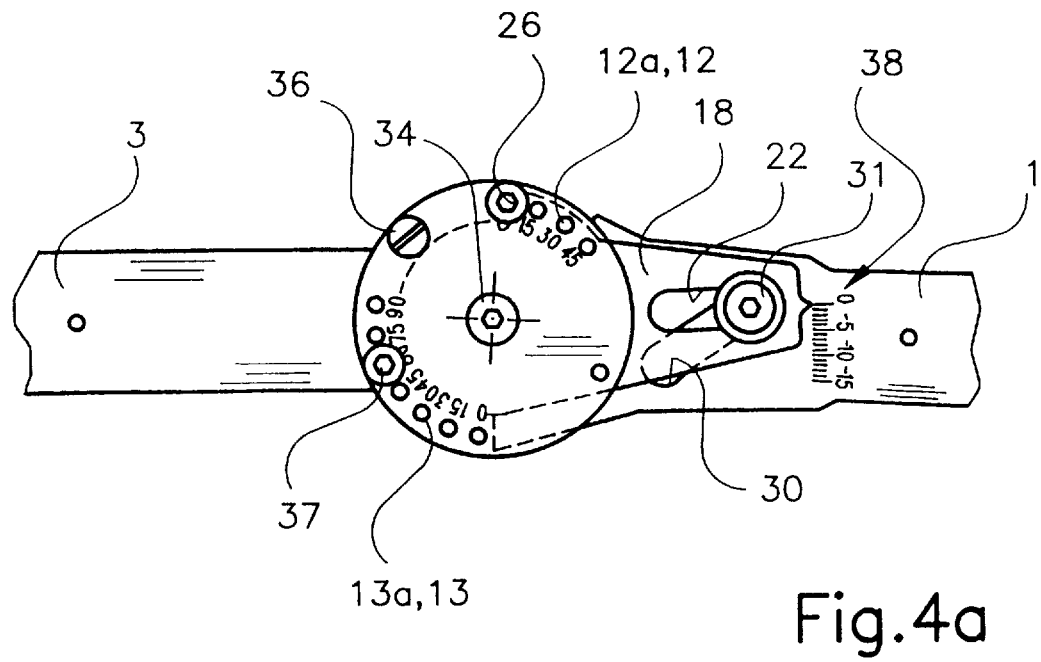
FIG. 4a is a side elevational view of the joint brace of FIG. 1 with a screw threaded washer in the 0° extension limiting position.
Figure 4B:
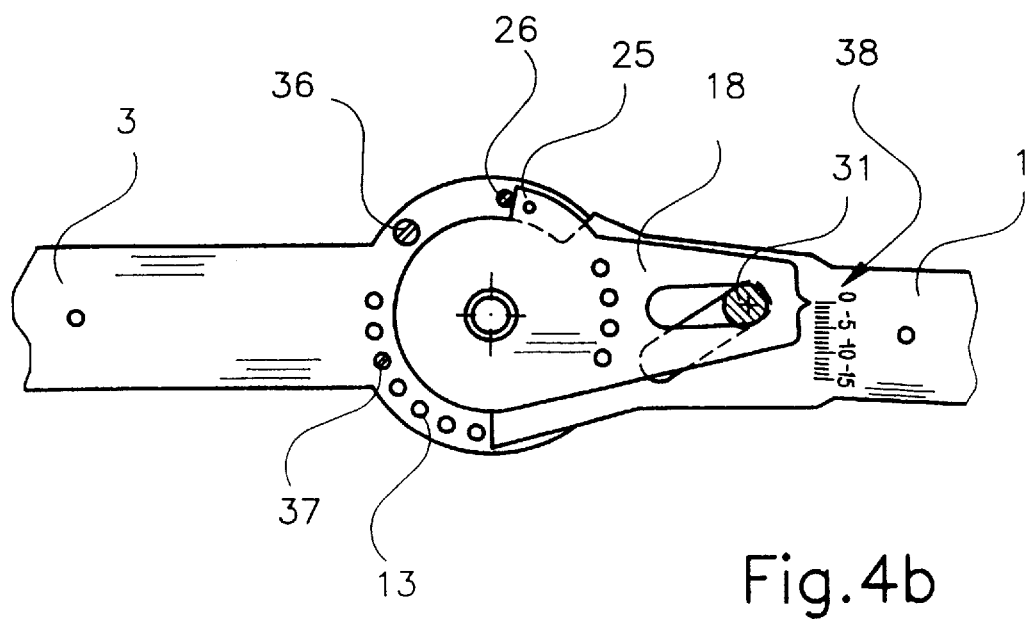
FIG. 4b is a side elevational view of the joint brace of FIG. 1 without a screw threaded washer in the 0° extension limiting position.

In FIGS. 4A and 4B the complementary abutment setting element 18 is so set on the distal splint 1 that the relative angle between these parts amounts to 0°. If the distal splint 1 is located in the illustrated maximum state of extension in relation to the proximal splint 3, the complementary abutment 25 of the complementary abutment setting element 18 will strike the extension abutment element 26, which is attached to the proximal splint 3 and the screw threaded disk 33 firmly connected with same. This condition is also indicate in the perspective view of FIG. 2.

Figure 5A:
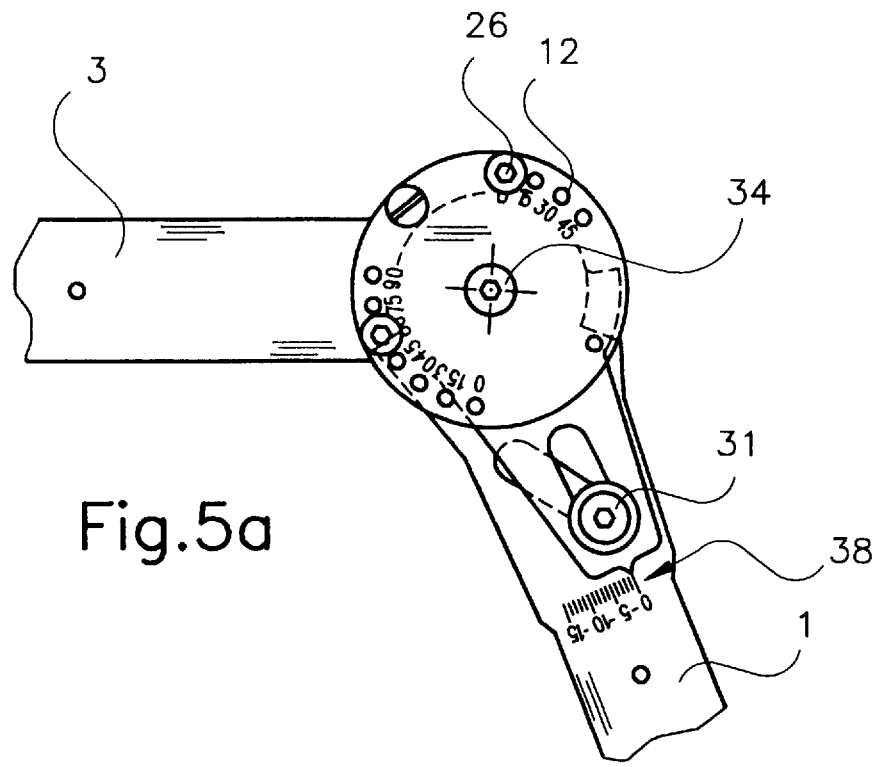
FIG. 5a is a side elevational view of the joint brace of FIG. 1 with a screw threaded washer in the 60° flexion limiting position.
Figure 5B:
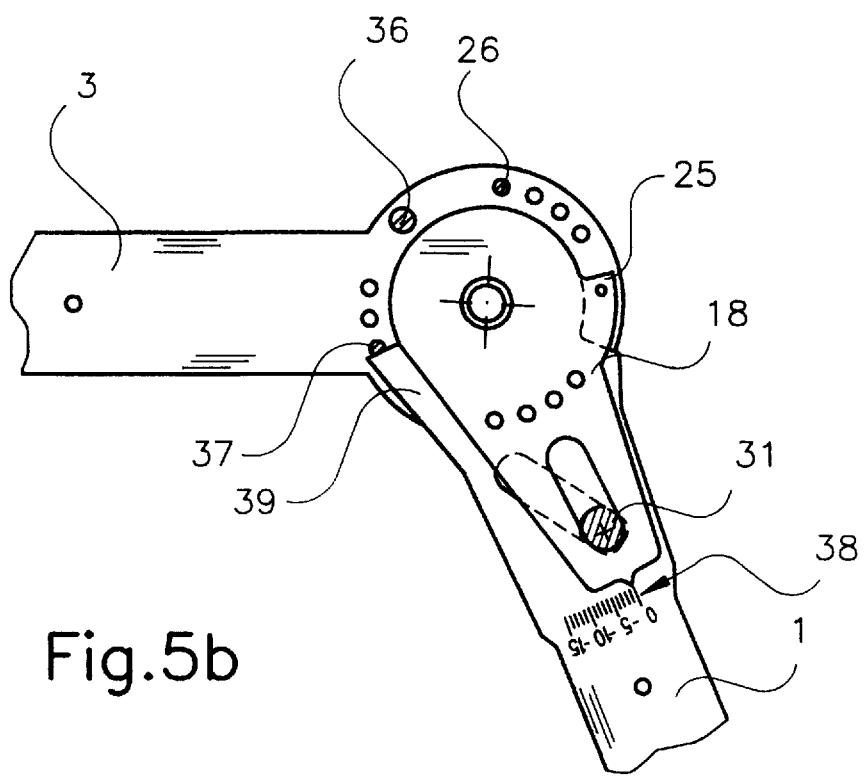
FIG. 5b is a side elevational view of the joint brace of FIG. 1 without a screw threaded washer in the 60° flexion limiting position.

Starting in this position it is possible for the distal splint 1 to be freely pivoted through any angle of 60° in the flexion direction until a flexion abutment 39, which is formed on the distal splint 1 strikes against the proximal splint 3. This position is represented in FIGS. 5A and 5B.

As will be seen, by insertion of the extension limiting abutment element 26 in the respective extension limiting holes 12 the maximum extension range may be set to 0°, 15°, 30° and, respectively, 45°. Simultaneously, by the insertion in the flexion abutment element 37 in the different flexion limiting holes 13 it is possible to set a flexion limit between 0° and 90° in steps of 15°.

Figure 6A:
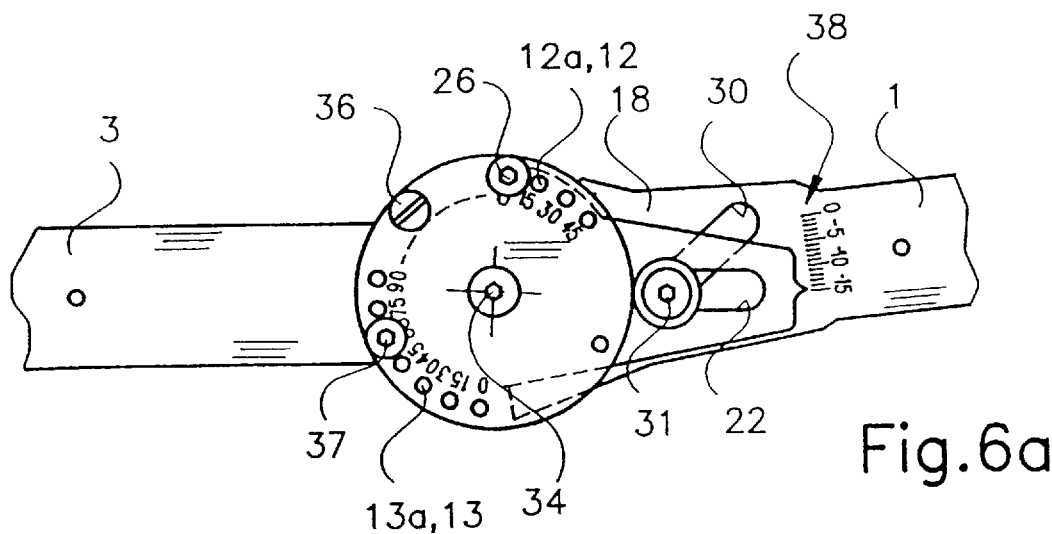
FIG. 6a is a side view of the joint brace of FIG. 1 with a screw threaded washer in the 15° extension limiting position (over-stretched position)
Figure 6B:
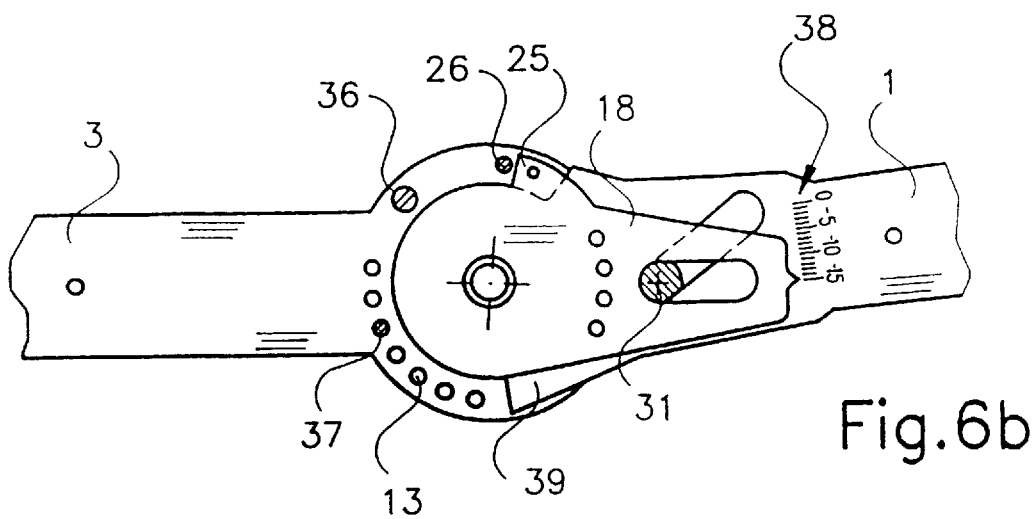
FIG. 6b is a side view of the joint brace of FIG. 1 without a screw threaded washer in the 15° extension limiting position (over-stretched position)

As shown in FIGS. 6A and 6B, owing to the complementary abutment setting element 18 of the invention it is possible, in addition to this adjustment in steps of the extension limit angle, to bring about a further stepless pivoting of the distal splint 1 in relation to the proximal splint 3 in a range of up to 15° in the extension direction. This is performed by releasing the guiding and setting element 31 so that even in a case in which the complementary abutment 25 is in contact with the extension abutment element 26, a further relative movement between the distal splint 1 and the complementary abutment setting element 18 is possible up to 15° in the extension direction. In this case the guiding and setting element 31 will move along the slots 22 and 30 toward the pivot axis 9 or, respectively, obliquely downward. If, as indicated in FIGS. 6A and 6B, an extension limit is desired in a over-stretch range of −15°, the guiding and setting element 31 is screwed fast in the −15° position on the distal splint 1 and the extension abutment element 26 is inserted into the 0° extension limit hole 12 in the proximal splint 3.

In order when screwing up the guiding and setting element 31 to avoid any undesired entrainment of the nut, same may possess a ledge with parallel side walls, which run with a small amount of play within the slot 30 in the distal splint 1.

Figure 7:
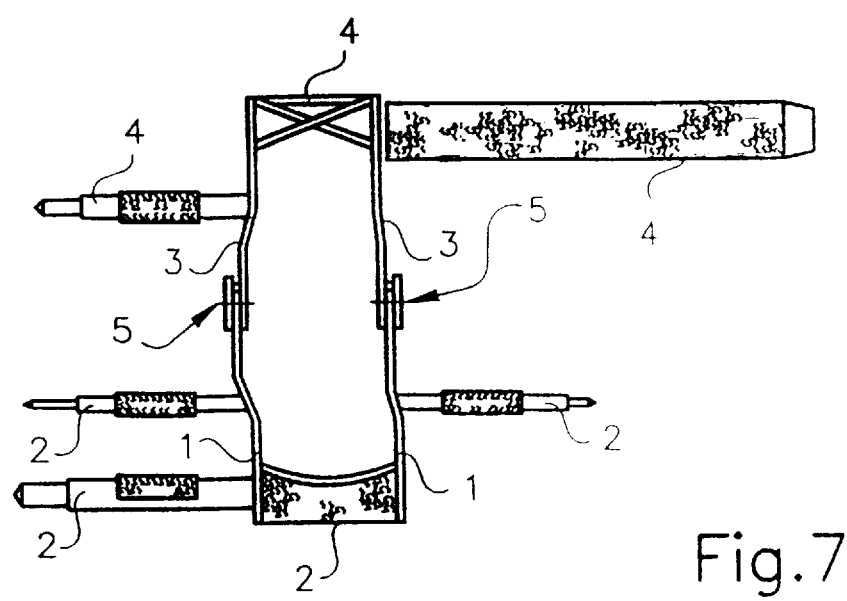
FIG. 7 is a diagrammatic front view of the entire joint brace in accordance with the invention.

In order to give an overall picture of the arrangement attention is called to FIG. 7, which represents a front view of the joint brace of the invention in a diagrammatic form. As is apparent, the attachment sections 1a and 3a of the distal splint 1 and, respectively, of the proximal splint 3 may be angled or cranked in a suitable fashion in order to provide for optimum adaptation in the joint region. For the attachment of the splints to the upper and, respectively, upper leg conventional straps 2 and 4, respectively, are employed.

Although the joint brace of the invention has been described in detail with reference to a knee orthosis, it is perfectly possible to employ such a joint brace for other purposes, for example on elbow or, in a smaller design, on finger joints. Furthermore it is readily possible to position the abutment not only for setting in the extension direction in a stepless manner over a given angular range in relation to the splint 1, but furthermore this also goes for the abutment in the flexion direction. Moreover, it is possible also to apply the complementary abutment setting element 18 in a steplessly adjustable manner not to the distal splint 1 but also to the proximal splint 3.

It will be understood that each of the elements described above, or two or more together, may also find a useful application in other types of braces differing from the types described above.

While the invention has been illustrated and described as embodied in the context of a joint brace and more particularly a knee brace, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

We claim:

1. A joint brace for preventing torsion of a distal extremity in relation to a proximal extremity connected articulatingly therewith, comprising splints (1 and 2) adapted to be attached to the distal and, respectively, proximal extremity, said splints being connected by means of a rotary joint (5), a free pivot range of the distal splint (1) in relation to the proximal splint (3) being able to be limited by means of an abutment element (26), which is adapted to be attached to one of the splints (1 and 3) and cooperates with a complementary abutment (25) of the other splint (1), said complementary abutment (25) being provided on a complementary abutment setting element (18) mounted in a rotatable manner for movement about the pivot axis (9) of the knee joint (8), wherein the abutment element (26) is adapted to be attached in predetermined, different positions to a joint section (3), adjacent to the pivot axis, of the splint (3), and wherein the complementary abutment setting element (18) comprises a pivoting lever, which pivoting lever is disposed adjacent to a manipulating section (21) extending past the joint section (3b) adjacent to the pivot axis and is able to be fixed by means of a guiding and setting element (31), adapted to be slid within a slot means (22 and 30), on the splint (1) associated with the complementary abutment setting element (18).

2. The joint brace as claimed in claim 1, characterized in that the manipulating section (21) of the complementary abutment setting element (18) and the splint (1) associated with the same, respectively possess a slot (22 and, respectively, 30), whose longitudinal axes intersect at a predetermined angle, and in that the guiding and setting element (31) extends through both slots (22 and 30) in the intersecting part thereof so that a displacement of the guiding and setting element (31) necessarily causes relative movement between the complementary abutment setting element (18) and the splint (1).

3. The joint brace as claimed in claim 2, characterized in that the slot (22) provided in the complementary abutment setting element (18) extends in the direction of the longitudinal axis of the manipulating section (21) and the slot (30) provided in the associated splint (1) includes an angle of 20° to 60° and more especially 35°, with the longitudinal axis of the splint (1).

4. The joint brace as claimed in claim 1, characterized in that the complementary abutment setting element (18) comprises at least one plate element of steel sheet.

5. The joint brace as claimed in claim 1, characterized in that the complementary abutment setting element (18) comprises two at least substantially identical halves (18a and 18b), same being arranged on either side of the associated splint (1).

6. The joint brace as claimed in claim 1, characterized in that the complementary abutment (25) on the complementary abutment setting element (18) is designed in the form of a projecting spur.

7. The joint brace as claimed in claim 1, characterized in that the guiding and setting element (31) is constructed in the form of a clamping screw.

8. The joint brace as claimed in claim 1, characterized in that the range of setting of the associated splint (1) in relation to the complementary abutment setting element (18) amounts to 0° to −20°, and more particularly 0° to −15°, in the extension direction, i. e. in the stretch out direction of the extremities in relation to the angular position as set by the extension abutment element(26).

9. The joint brace according to claim 1, wherein the joint brace is a knee joint brace.

10. A joint brace for a knee formed by a distal extremity and by a proximal extremity comprising a distal splint adapted to be attached to the distal extremity;

a proximal splint adapted to be attached to the proximal extremity;

a rotary joint connecting the distal splint to the proximal splint;

a first abutment element adapted to be attached to a member of the group selected from the distal splint and the proximal splint;

a second abutment element adapted to be attached to a member of the group selected from the distal splint and the proximal splint such that each splint is associated with one of the abutment elements, wherein the first abutment element cooperates with the second abutment element, and wherein a free pivot range of the distal splint in relation to the proximal splint is able to be limited by means of the first abutment element;

an abutment setting element, wherein said second abutment element is provided on the abutment setting element and mounted in a rotatable manner for movement about a common axis with a pivot axis of a knee joint;

a joint section disposed adjacent to the pivot axis of the respective splint, wherein the first abutment element is adapted to be attached in predetermined, different positions to the joint section of the respective splint;

a manipulating section extending past the joint section adjacent to the common axis, wherein the abutment setting element comprises a pivoting lever, wherein the pivoting lever is disposed adjacent to the manipulating section;

a guiding and setting element, wherein the pivoting lever is able to be fixed by means of the guiding and setting element;

slot means disposed on the splint associated with the abutment setting element, and wherein the guiding and setting element is adapted to be slid within the slot means for preventing torsion of the distal extremity in relation to the proximal extremity connected articulatingly with the distal extremity.

11. The joint brace as claimed in claim 10, wherein the manipulating section of the abutment setting element possesses a first slot, and wherein the splint associated with the abutment setting element possesses a second slot, wherein the longitudinal axis of the first slot intersects the longitudinal axis of the second slot at a predetermined angle, and wherein the guiding and setting element extends through the first slot and through the second slot in the intersecting part of the first slot and of the second slot such that a displacement of the guiding and setting element necessarily causes a relative movement between the abutment setting element and the overlapping splint.

12. The joint brace as claimed in claim 11, wherein the first slot provided in the abutment setting element extends in the direction of the longitudinal axis of the manipulating section, and wherein the second slot provided in the associated splint includes an angle of from about 20° to 60° relative to the longitudinal axis of the associated splint.

13. The joint brace as claimed in claim 9, wherein the first slot provided in the abutment setting element extends in the direction of the longitudinal axis of the manipulating section, and wherein the second slot provided in the associated splint includes an angle of about 35° relative to the longitudinal axis of the associated splint.

14. The joint brace as claimed in claim 10, wherein the abutment setting element comprises at least one plate element of steel sheet.

15. The joint brace as claimed in claim 10, wherein the abutment setting element comprises two at least substantially identical halves, same being arranged on either side of the associated splint.

16. The joint brace as claimed in claim 10, wherein an abutment on the abutment setting element is designed in the form of a projecting spur.

17. The joint brace as claimed in claim 10, wherein the guiding and setting element is constructed in the form of a clamping screw.

18. The joint brace as claimed in claim 10, wherein a range of setting of the associated splint in relation to the abutment setting element amounts to 0° to −20° in an extension direction, i.e. in a stretch out direction of extremities in relation to an angular position as set by the abutment setting element.

19. The joint brace as claimed in claim 10, wherein a range of setting of the associated splint in relation to the abutment setting element amounts to 0° to −15°, in an extension direction, i.e. in a stretch out direction of extremities in relation to an angular position as set by the abutment setting element.

* * * * *